(12) United States Patent
Drnevich et al.

(10) Patent No.: US 7,040,145 B2
(45) Date of Patent: May 9, 2006

(54) METHOD AND APPARATUS FOR MEASURING DRY DENSITY AND WATER CONTENT OF SOIL

(75) Inventors: Vincent P. Drnevich, West Lafayette, IN (US); Xiong Yu, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 10/779,899

(22) Filed: Feb. 17, 2004

(65) Prior Publication Data

US 2004/0201385 A1 Oct. 14, 2004

Related U.S. Application Data

(60) Provisional application No. 60/448,063, filed on Feb. 18, 2003.

(51) Int. Cl.

| | |
|---|---|
| G01N 25/56 | (2006.01) |
| G01N 5/02 | (2006.01) |
| G01R 27/04 | (2006.01) |
| G01R 27/32 | (2006.01) |

(52) U.S. Cl. .......................................... 73/73; 324/643
(58) Field of Classification Search ................ 73/32 R, 73/73; 324/643, 642, 637, 689, 690
See application file for complete search history.

(56) References Cited

U.S. PATENT DOCUMENTS

| 5,136,249 A | 8/1992 | White et al. .................. 324/643 |
| 5,646,537 A * | 7/1997 | Skaling et al. ............... 324/643 |
| 5,801,537 A * | 9/1998 | Siddiqui et al. ............. 324/643 |
| 5,933,015 A * | 8/1999 | Siddiqui et al. ............. 324/643 |
| 6,215,317 B1 * | 4/2001 | Siddiqui et al. ............. 324/643 |

FOREIGN PATENT DOCUMENTS

JP 62289761 A * 12/1987

OTHER PUBLICATIONS

Siddiqui, S.I., Drnevich, V.P. and Deschamps, R.J., "Time Domain Reflectometry Development for Use in Geotechnical Engineering," *Geotechnical Testing Journal*, GTJODJ, vol. 23, No. 1, Mar. 2000, pp. 9-20.

(Continued)

*Primary Examiner*—Hezron Williams
*Assistant Examiner*—Tamiko Bellamy
(74) *Attorney, Agent, or Firm*—William F. Bahret; P. Derek Pressley

(57) ABSTRACT

A method and apparatus for measuring dry density and gravimetric water content of soil includes the steps of providing a plurality of spikes adapted to be driven into the soil and driving the spikes into the soil in spaced relationship. An electrical signal is applied to the spikes and a reflected signal is analyzed using time domain reflectometry to determine an apparent dielectric constant and the bulk electrical conductivity of the soil. With these parameters, the dry density and gravimetric water content of the soil can be calculated using a predetermined relationship between apparent dielectric constant, bulk electrical conductivity, dry density and gravimetric water content. The predetermined relationship includes experimentally determined soil specific calibration constants. The calculated value of the bulk electrical conductivity as determined by time domain reflectometry is adjusted to correspond to a value for which values of the constants are known. The value of the apparent dielectric constant is adjusted to compensate for temperature.

38 Claims, 10 Drawing Sheets

OTHER PUBLICATIONS

Drnevich, V.P., Lin, C. P., Yi, Q., Yu, X. and Lovell J. "Real-Time Determination of Soil Type, Water Content and Density Using Electromagnetics", Technical Summary, Report No.: FHWA/IN/JTRP-2000-20, Joint Transportation Research Program, Indiana Department of Transportation—Purdue University, Aug. 2001, 3 p.

Drnevich, V.P., Yu. X., and Lovell, J., "A New Method for Water Content and In Situ Density Determination," Proceedings of the Great Lakes Geotechnical and Geoenvironmental Conference, Toledo, Ohio, May 2002, 16p.

Ferre, P.A.., Rudolph, D.L., Kachanoski, R.G., "Spatial Averaging of Water Content by Time Domain Reflectory: Implications For Twin Rod Probes With And Without Dielectric Coating," *Water Resource Research*, vol. 32, 1996 pp. 271-279.

Amente, G., Baker, J. M. and Reece, F. C., "Estimation of Soil Solution Electrical Conductivity from Bulk Soil Electric Conductivity in Sandy Soils," *Soil Sci. Soc. Am. J.* vol. 64, 2000, pp. 1931-1939.

Drnevich, V.P., Yu. X., Lovell, J., and Tishmack, J.K., "Temperature Effects on Dielectric Constant Determined by Time Domain Reflectometry," TDR 2001: Innovative Applications of TDR Technology, Infrastructure Technology Institute, Northwestern University, Evanston, IL, Sep. 2001, 10 p.

Rinaldi, A. V. and Cuestas, A.G., "Ohmic Conductivity of a Compacted Silty Clay," *Journal of Geotechnical and Geoenvironmental Engineering*, vol. 128, No. 10, 2002, pp. 824-835.

\* cited by examiner

METHOD AND APPARATUS FOR MEASURING DRY DENSITY AND WATER CONTENT OF SOIL

CROSS-REFERENCE TO RELATED APPLICATION

This application claims the benefit of U.S. Provisional Patent Application Ser. No. 60/448,063, filed Feb. 18, 2003, which application is hereby incorporated by reference.

TECHNICAL FIELD OF THE INVENTION

The present invention relates generally to methods and apparatus for measuring soil parameters and, more particularly, to methods and apparatus for measuring dry density and water content of soil using time domain reflectometry.

BACKGROUND OF THE INVENTION

Time domain reflectometry (TDR) has been used to measure the volumetric moisture content of soils (volume of moisture per unit volume of soil), mostly in the field of soil science. As shown in FIG. 1, these measurements involved the insertion of a probe 10 comprising a central rod 12 and two or more peripheral rods 14 into the soil 16 to be measured. The peripheral rods 14 (which are preferably three in number) are spaced equidistant from the central rod 12 and equidistant from each other. A coaxial transmission line 18 is then coupled to the structure with the center conductor of the coaxial cable 18 coupled to the center rod 12 and the exterior shield (outer conductor) of the coaxial cable 18 coupled to each of the peripheral rods 14. In this way, the peripheral rods 14 simulate the effects of a continuous outer coaxial shield in the soil 16, without the requirement of attempting to drive a cylindrical probe into the soil 16. Time domain reflectometry analysis equipment 20 is then coupled to the coaxial cable 18, and the reflections of high frequency electrical signals from the soil 16 are measured using the analysis equipment 20. These reflections will change in predictable ways depending upon the dielectric constant of the soil 16, which has been found to be strongly correlated with the volumetric moisture content of the soil 16. Therefore, time domain reflectometry has been established as a viable tool for measuring volumetric moisture content of a soil.

An innovative improvement was made by Siddiqui and Drnevich, U.S. Pat. Nos. 5,801,537; 5,933,015; and 6,215,317, which are hereby incorporated by reference, to extend TDR to geotechnical applications.[1] They developed a calibration equation relating soil apparent dielectric constant to soil gravimetric water content and dry density and designed procedures for laboratory calibration and field application. The laboratory calibration was done in conjunction with a standard compaction test. The field procedure consisted of two tests: 1) a test in which a TDR reading was taken on a plurality of spikes driven into the soil; and 2) a test in which a TDR reading was taken in a compaction mold on the same soil that was rapidly excavated from within the volume bounded by the spikes. The spikes formed a coaxial probe for the first test and a single rod driven into the center of the soil in the compaction mold formed a coaxial mold probe for the second test. Assuming that the water content was the same for both tests, the apparent dielectric constant from the two TDR readings and the measured total density of the soil in the mold were used to calculate soil water content and dry density. Laboratory and field evaluations indicated that the method had sufficient accuracy for geotechnical purposes.[2,3,4,5] An ASTM standard designated ASTM D6780 for the method was recently approved. The procedure described above made use of measured apparent dielectric constants (one with soil in place and one with soil in the mold). It also required digging out the soil and compacting it into a mold. This process required about 10 to 15 minutes.

[1] Siddiqui, S. I. and Drnevich, V. P. (1995). "A New Method of Measuring Density and Moisture Content of Soil Using the Technique of Time Domain Reflectometry," Report No.: FHWA/IN/JTRP-95/9, Joint Transportation Research Program, Indiana Department of Transportation—Purdue University, February, 271 p.

[2] Lin, C. P. (1999), "Time domain reflectometry for soil properties", Ph.D. Thesis, School of Civil Engineering, Purdue University, West Lafayette, Ind.

[3] Siddiqui, S. I., Drnevich, V. P. and Deschamps, R. J. (2000). "Time Domain Reflectometry Development for Use in Geotechnical Engineering," Geotechnical Testing Journal, GTJODJ, Vol. 23, No. 1, March, pp. 9–20.

[4] Drnevich, V. P., Lin, C. P., Yi, Q., Yu, X. and Lovell J. (2001b), "Real-time determination of soil type, water content and density using electromagnetics", Report No.:FHWA/IN/JTRP-2000-20, Joint Transportation Research Program, Indiana Department of Transportation—Purdue University, August, 288 p.

[5] Drnevich, V. P., Yu, X., and Lovell, J., 2002, A New Method for Water Content and Insitu Density Determination, Proceedings of the Great Lakes Geotechnical and Geoenvironmental Conference, Toledo, Ohio, May, 15p A multiple rod probe (MRP) 22 of the prior art according to Siddiqui and Drnevich is illustrated in FIGS. 2–4. The MRP 22 was used to measure the dielectric constant (and hence the volumetric moisture content) of an in-place soil sample. The conducting rods 24 of the MRP 22 were driven into the soil 26 in a predetermined pattern using a guide template 28 placed upon the surface of the soil. The pattern included a centrally located rod and two or more peripherally located rods, all being equidistant from the central rod. The rods 24 were preferably common metal spikes, and extended into the soil to a depth of approximately nine inches. The template 28 was removed after the rods 24 were driven into the soil. The MRP 22 further included an interface cap 30 which was formed from a conductive material, such as stainless steel. The cap 30 had a plurality of studs 32 extending downwardly therefrom. The centrally located stud was electrically insulated from the interface cap 30, while the peripheral studs were mounted in electrical contact with the conductive portion of the cap 30. A coaxial connector 34 was mounted to the cap 30 such that the outer conductor was in electrical contact with the conductive portion of the cap 30 and the peripherally located studs 32. The center conductor of the connector 34 was in electrical contact with the centrally located stud but was insulated from the conductive portion of the cap 30. The connector 34 was coupled to a TDR instrument 20 by means of a coaxial cable 18.

It would be a desirable improvement to the above-described prior method and apparatus to make use of only the multiple rod probe, and eliminate the necessity of excavating and compacting soil into a compaction mold in the field. The present invention provides this and other desirable improvements.

SUMMARY OF THE INVENTION

The present invention relates to a method and apparatus for determining gravimetric water content and dry density of soil in place. This invention makes use of the principle of time domain reflectometry (TDR) associated with electromagnetic waves traveling in a medium. A multiple rod probe is designed to contact spikes driven into the ground to measure a TDR signal applied to the soil in place. Two measurements are made on the TDR signal from a single test sample. One measurement determines the apparent dielectric constant and the other measurement determines the bulk electrical conductivity. The invention makes use of a newly discovered relationship wherein apparent dielectric constant and bulk electrical conductivity are functions of gravimetric water content and dry density.

Dielectric constant and bulk soil electrical conductivity are measured simultaneously on the same soil sample. Calibration equations correlate these two parameters with soil gravimetric water content and dry density, which equations are simultaneously solved after adjusting field-measured conductivity to a standard conductivity. The method compensates for temperature effects. Testing may be done on soil in place using a special probe that obtains average values over a fixed depth from the surface.

BRIEF DESCRIPTION OF THE DRAWINGS

In FIG. 5a, dry density is constant and gravimetric water content varies. In FIG. 5b, gravimetric water content is constant and dry density varies.

FIG. 8a shows clayed soil, PL=20, LL=32. FIG. 8b shows ASTM graded sand with differing amounts of salt in the pore water.

DESCRIPTION OF THE PREFERRED EMBODIMENT

Figure 1:
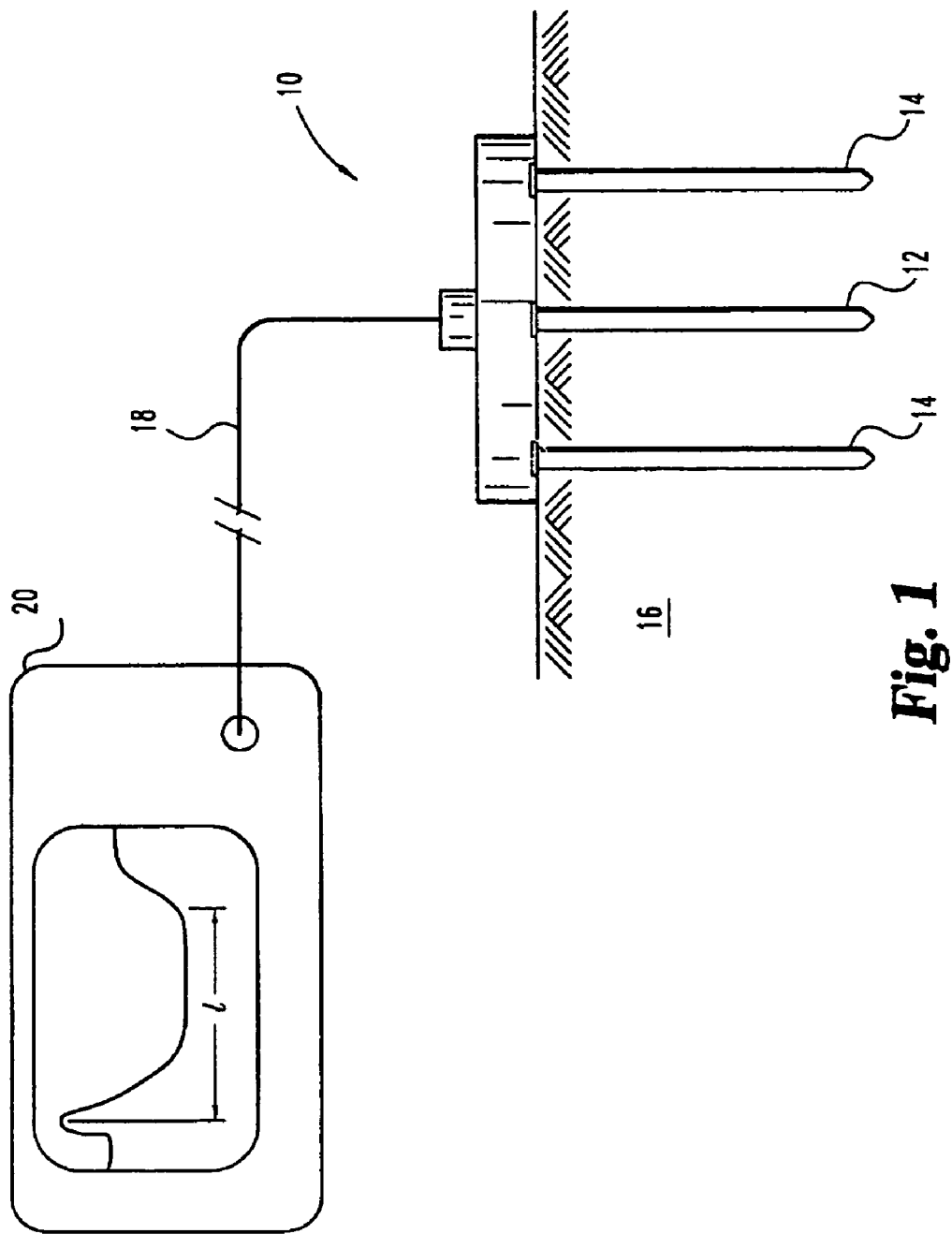
FIG. 1 is a side elevational view of a prior art probe for measuring the dielectric constant of an in-place soil sample.
Figure 2:
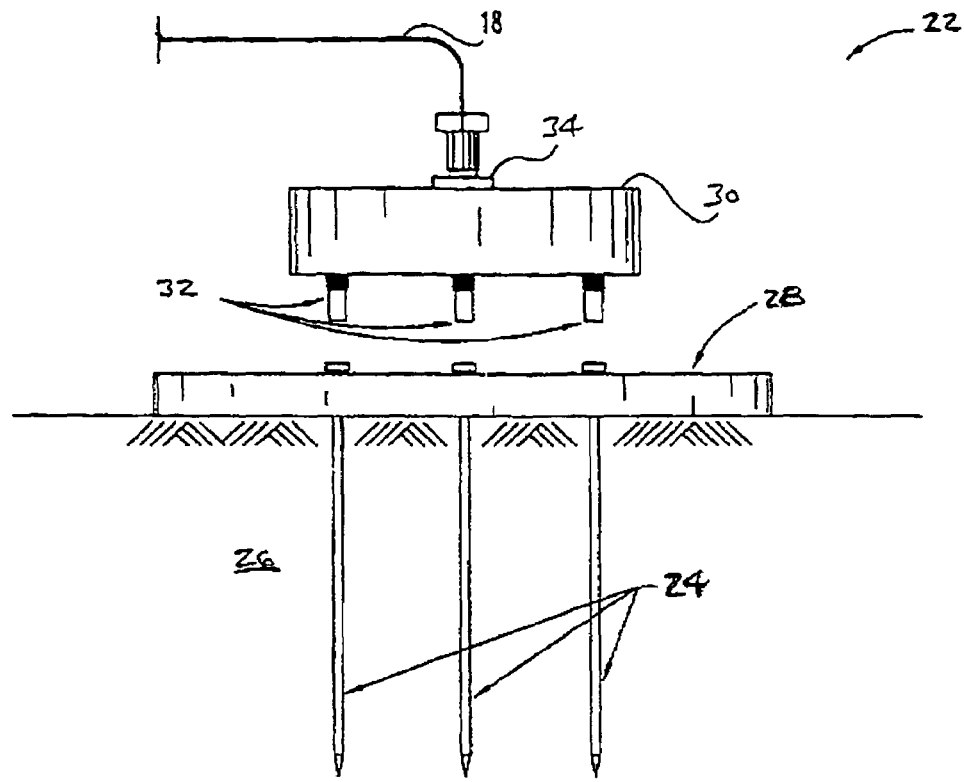
FIG. 2 is a side elevational view of another prior art multiple rod probe, illustrated in use with a template and spikes.
Figure 3:
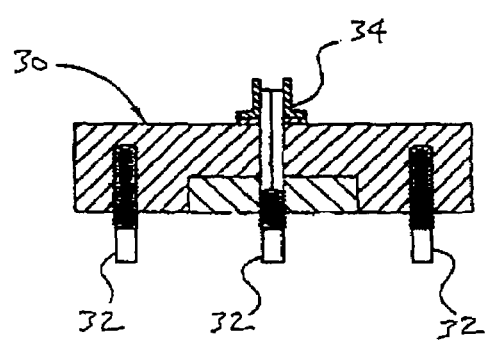
FIG. 3 is a cross-sectional view of the multiple rod probe of FIG. 2.
Figure 4:
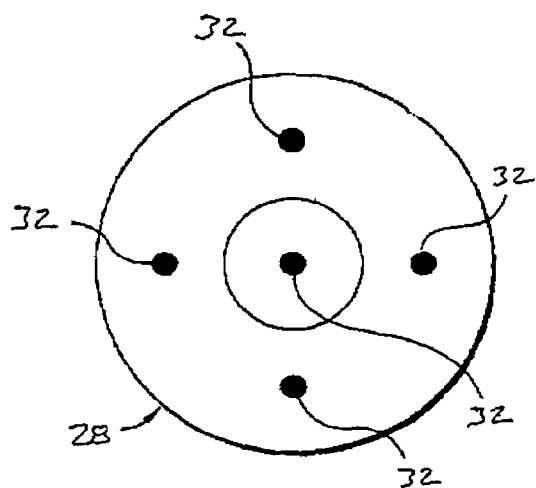
FIG. 4 is a bottom plan view of the multiple rod probe of FIG. 2.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Compaction quality control is important for engineered earthwork construction. Soil water content and dry density are properties generally used for controlling compaction quality. Currently used methods, including nuclear methods, obtain total density with one procedure and the water content with a different procedure, which are independent of each other. In most cases, these measurements are made on different "samples" of soil. Dry density is then calculated. The TDR method described herein determines water content and dry density directly from one measurement on the same soil sample in place. The reference method for water content measurement is the oven-dry method (ASTM D2216), which requires accurate sampling and oven drying for 24 hours. There is no reference method for density determination in place at this time.

Time domain reflectometry (TDR) technology has been shown to be a reliable, fast, and safe technology for field monitoring of the volumetric water content of soil, i.e., volume of water compared to total volume. A universal relation between soil volumetric water content and soil apparent dielectric constant has been established. In addition to soil apparent dielectric constant, it also is possible to obtain bulk soil electrical conductivity from TDR waveforms.

Geotechnical applications require the gravimetric water content, i.e. mass of water compared to mass of soil solids. Gravimetric water content is related to volumetric water content by the dry density of the soil. The term "water content" as used herein refers to gravimetric water content unless explicitly stated otherwise.

The present invention provides an improved method and apparatus that makes use of only one field TDR measurement to determine bulk soil electrical conductivity in addition to apparent dielectric constant to obtain soil water content and dry density. Thus no soil needs to be excavated during field testing and the testing time is reduced to a few minutes.

Figure 5A:
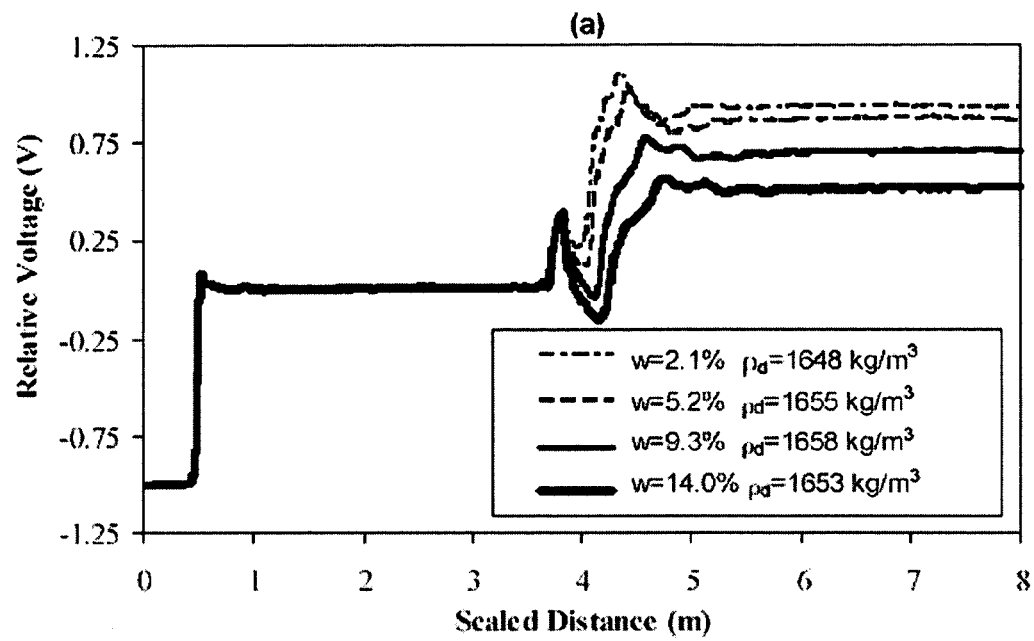
FIGS. 5a and 5b show the influence of soil properties on a TDR waveform.
Figure 5B:
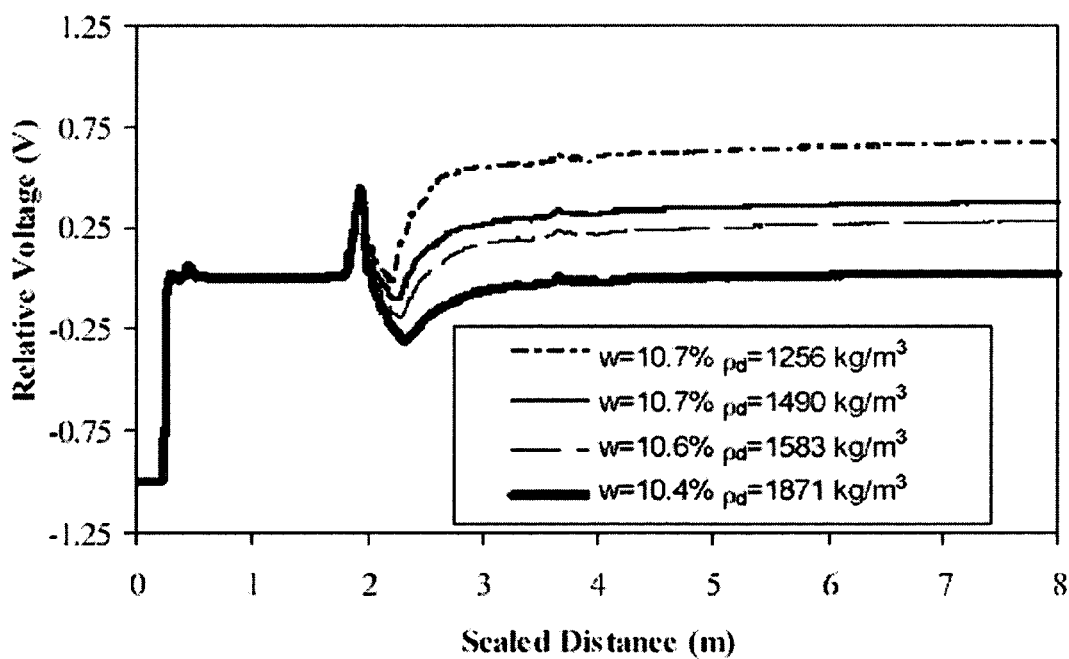

TDR measures soil apparent dielectric constant through measuring the speed of an electromagnetic wave traveling in soil. Apparent dielectric constant is given by $$K_a = \left(\frac{L_a}{L_p}\right)^2 \quad (1)$$

where $L_a$ is the distance between reflections (called apparent length) and $L_p$ is the length of the probe. For TDR measurements in soil, electromagnetic reflections occur as the wave reaches the soil surface and again as the wave reaches the end of the probe as shown in FIGS. 5a and 5b. The apparent length is the measured distance between these two reflections points. As water content or density increases, the apparent length also increases.

Various methods have been proposed to pick the two reflection points from TDR waveforms, among which the tangent line method is most widely used. We developed a robust algorithm using the concept of curvature to identify the reflection points for the present method.

Figure 6:
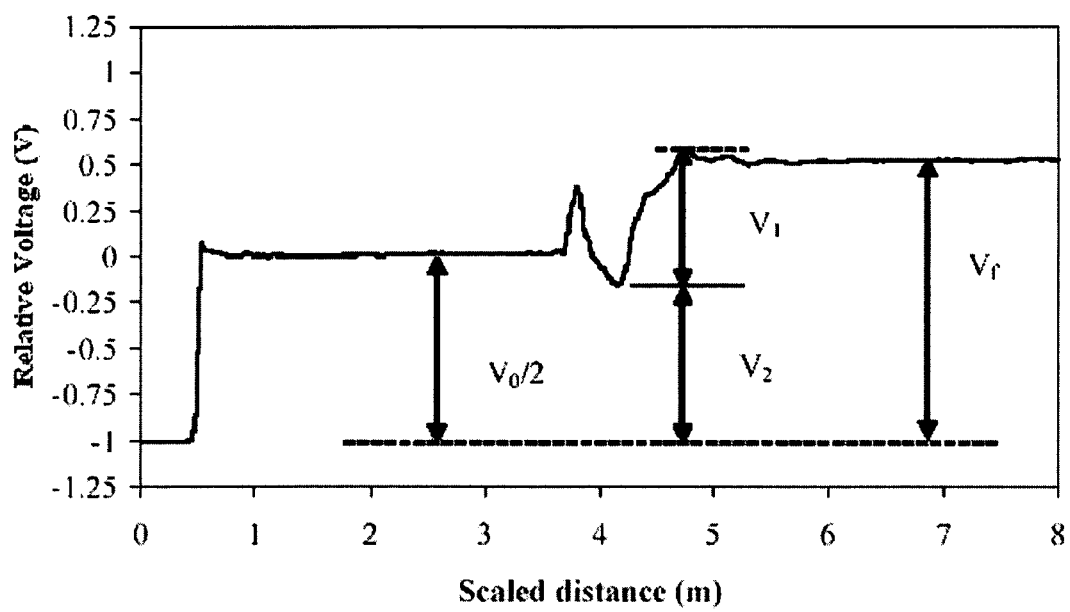
FIG. 6 shows the definitions of different voltage levels for a TDR waveform.

The electrical conductivity of a soil material causes attenuation of the TDR waveform. This phenomenon is described by transmission line theory. An analysis technique using the concept of TDR wave attenuation in a transmission line is known. The bulk electrical conductivity is expressed in terms of the voltage level that occurs after the reflection from the end of the probe $$EC_b = \frac{K_a^{1/2}}{120\pi L_p} \ln\left(\frac{V_1}{V_2}\right) \quad (2)$$

where $EC_b$ is the bulk electrical conductivity, $K_a$ is the apparent dielectric constant, $L_p$ is the probe length, and $V_1$ and $V_2$ are voltage levels, as shown in FIG. 6. This approach was later found to not account for effects of the intervening coaxial cable and the impedance matching transformer.

Additional shortcomings of this model are:
1) $EC_b$ is coupled with $K_a$, which might be a source of error;
2) Picking accurate values of $V_0$, $V_1$, $V_f$ could be difficult.

Analysis of the long-term response of a transmission line indicates the bulk electrical conductivity can be calculated from the TDR voltage level at long times using a simplified static circuit analysis $$EC_b = \frac{1}{C}\left(\frac{V_s}{V_f} - 1\right) \quad (3)$$

where $V_s$ is the source voltage which equals twice the step pulse, $V_f$ is the long term voltage level, and C is a constant related to probe configuration. For coaxially configured probes, $$C = \frac{2\pi L_p R_s}{\ln\left(\frac{d_o}{d_i}\right)},$$

where $L_p$ equals the probe length in soil, $R_s$ the internal resistance of the pulse generator, and $d_o$ and $d_i$ are outer and inner conductor diameters, respectively.

Figure 7:
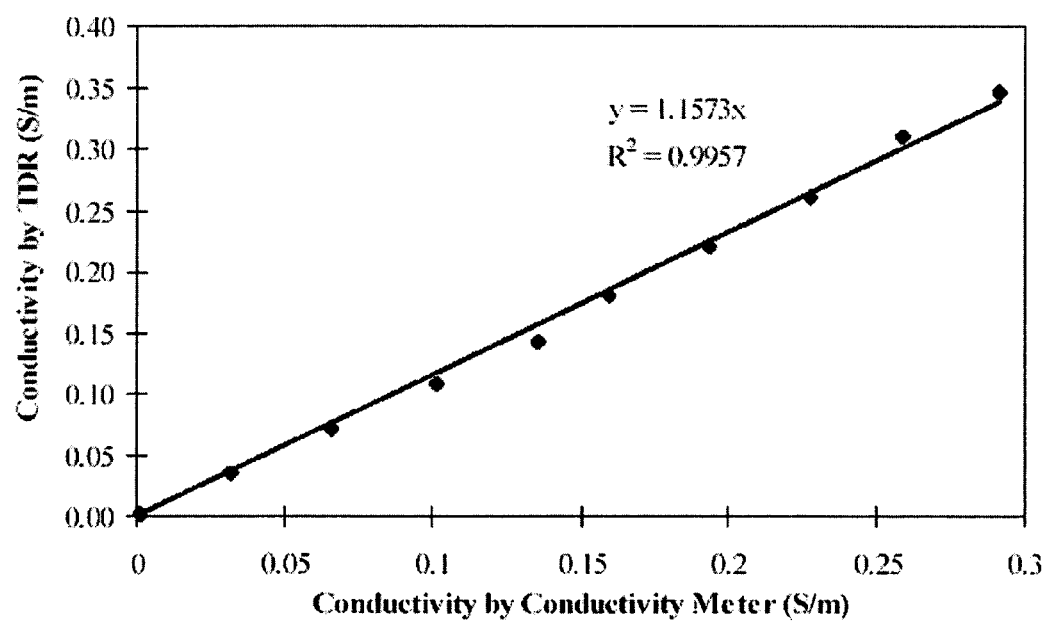
FIG. 7 shows the correlation between conductivity measured by TDR and conductivity measured by a conductivity meter.

This approach had been proposed for analyzing dielectric behavior of thin samples, and it was found that applying this approach for bulk soil electrical conductivity produced satisfactory results. We used this method for the measurement of the conductivity of water with various amounts of salts added to increase ionic conductivity. Results showed a good linear relationship with conductivity measured with a bench conductivity meter (FIG. 7). Equation 3 is used in the method of the present invention described herein to obtain bulk soil electrical conductivity from TDR measurements.

Due to the large dielectric constant for water (around 80 at 20° C.) in contrast to the relatively small dielectric constant for soil solids (around 3 to 5), it is possible to relate soil apparent dielectric constant to soil water content. The relationships are called calibration equations.

It was known that for soils with a wide range of mineral content, a single equation was adequate and was practically independent of soil bulk density, ambient temperature, and salt content. That relation is now widely used as a calibration curve and is referred to as Topp's equation, $$\theta = 4.3 \times 10^{-6} K_a^3 - 5.5 \times 10^{-4} K_a^2 + 2.92 \times 10^{-2} K_a - 5.3 \times 10^{-2} \quad (4)$$

This calibration equation has been confirmed by numerous authors on various soils and currently is the most widely used calibration equation for TDR applications.

However, it is observed that for organic soils, fine-textured soils, and clays, the dependency of $K_a$ on $\theta$ differs from Topp's equation. The deviation is attributed to soil density and texture (bound water) effects.

Experiments by others on eight different types of soil indicate that the deviation from Topp's equation appears more due to density effects than to bound water effects. Others incorporated bulk dry density, percent clay content, and percent organic content to get an improved general calibration relation. They also showed that the improved accuracy in volumetric water content was mostly attributed to the dry density term.

Another popular type of calibration is based upon a linear relationship between $\sqrt{K_a}$ and $\theta$.

$$\theta = b\sqrt{K_a} + a \quad (5)$$

in which a and b are constants obtained by regression. However, Eq. 5 does not account for soil density effects. A calibration equation incorporating density effects was also proposed.

$$\theta = \frac{K_a^{0.5} - 0.819 - 0.618\rho_b + 0.159\rho_b^2}{7.17 + 1.18\rho_b} \quad (6)$$

There also exists a calibration relationship based on theoretical polarization analysis of dielectric mixtures.

Two factors make it difficult to apply these calibration equations to geotechnical practice:
1) The calibrations are expressed in terms of volumetric water content and independent determination of dry density is needed to obtain gravimetric water content;
2) The improved calibrations accounting for bulk density effects are complex in form and hard to apply.

Another proposed calibration equation utilized the concept of gravimetric water content along with soil dry densities $$\sqrt{K_a}\frac{\rho_w}{\rho_d} = a + bw \quad (7)$$

where $p_w$ is the density of water, $P_d$ is the dry density of soil, a and b are soil specific calibration constants, and w is the gravimetric water content.[1,3]

[1] Siddiqui, S. I. and Drnevich, V. P. (1995). "A New Method of Measuring Density and Moisture Content of Soil Using the Technique of Time Domain Reflectometry," Report No.: FHW A/IN/JTRP-95/9, Joint Transportation Research Program, Indiana Department of Transportation—Purdue University, February, 271 p.

[3] Siddiqui, S. I., Drnevich, V. P. and Deschamps, R. J. (2000). "Time Domain Reflectometry Development for Use in Geotechnical Engineering," Geotechnical Testing Journal, GTJODJ, Vol. 23, No. 1, March, pp. 9–20.

A close inspection of this expression shows that it is consistent with the relationship obtained using volumetric mixing formulas.[2] This calibration equation can be converted to one for volumetric water content by use of

[2] Lin, C. P. (1999), "Time domain reflectometry for soil properties", Ph.D. Thesis, School of Civil Engineering, Purdue University, West Lafayette, Ind.

$$\theta = w\frac{\rho_d}{\rho_w} \quad (8)$$

which gives $$\sqrt{K_a} = a\frac{\rho_d}{\rho_w} + b\theta \qquad (9)$$

From Eq. 9, when θ=0 (dry soil), $$a = \sqrt{K_{a,s}}\frac{\rho_w}{\rho_d};$$

when θ=100 percent (pure water), b=$\sqrt{K_{a,w}}$. Thus a is the $\sqrt{K_{a,s}}$ (refraction index of soil solids) normalized by soil dry density; b is $\sqrt{K_{a,w}}$ (refraction index of pore fluid).[5]

Figure 8A:
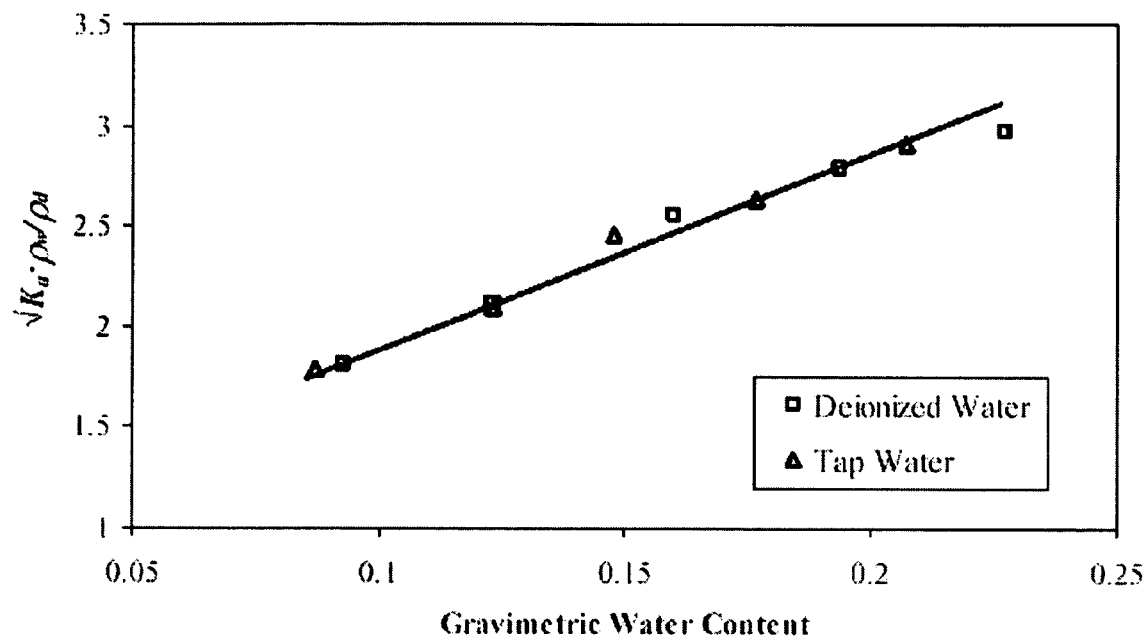
FIGS. 8a and 8b show the calibration of dielectric constant for different pore fluids.
Figure 8B:
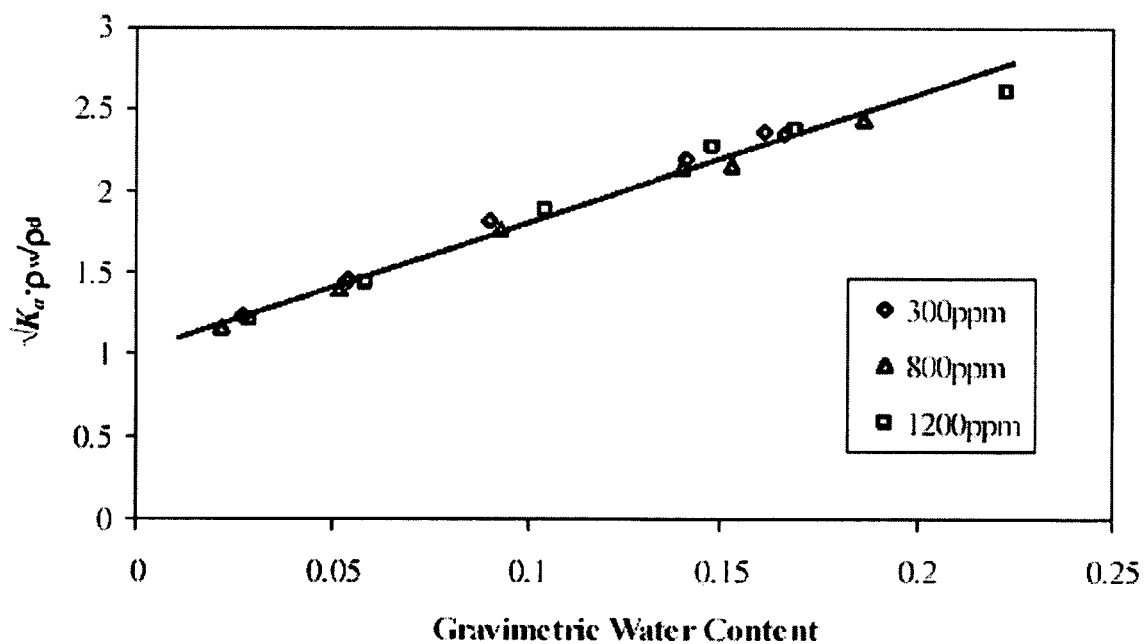

[5] Drnevich, V. P., Yu, X., and Lovell, J., 2002, A New Method for Water Content and Insitu Density Determination, Proceedings of the Great Lakes Geotechnical and Geoenvironmental Conference, Toledo, Ohio, May, 15p According to the procedure described in ASTM D6780 the calibration constants a and b are obtained in conjunction with the standard compaction test (ASTM D698 or ASTM D1557). Use of commonly accepted values for $K_{a,s}$ and extreme ranges of dry density show that the variation of a is from 0.5 to 1.85. The typical value of $K_{a,w}$ is about 81 at 20° C. which gives a value of b of approximately 9.[5] It is also observed that the calibration for dielectric constant is insensitive to pore-fluid conductivity for both sandy and clayed soils (FIGS. 8a and 8b).

[5] Drnevich, V. P., Yu, X., and Lovell, J., 2002, A New Method for Water Content and Insitu Density Determination, Proceedings of the Great Lakes Geotechnical and Geoenvironmental Conference, Toledo, Ohio, May, 15p As stated above, bulk soil electrical conductivity can be obtained from analysis of TDR waveforms by use of Eq. 3. The next task is to relate bulk soil electrical conductivity to soil physical properties.

Because soil is a three-phase system, factors influencing soil electrical conductivity include: porosity, degree of saturation, composition of pore water, mineralogy, soil structure, etc. General theoretical equations expressing the electrical conductivity as a finction of all these factors are not available because of the inherent complexity of the soil-water system in most natural soils. However, a number of empirical equations and theoretical expressions based upon simplified models are available that give satisfactory results for given conditions.

An important observation on bulk soil electrical conductivity from laboratory tests is that for a given soil water content, bulk electrical conductivity is proportional to soil pore fluid electrical conductivity. This leads to Archie's law, in which bulk soil electrical conductivity is expressed as a function of pore fluid conductivity, porosity, degree of saturation, etc. Conductivity by soil particles is ignored and thus the relationship is only applicable for coarse materials.

An improved relationship based on a two-pathway model which took into consideration both the conduction by pore fluid and the conduction via surfaces of soil particles was developed, $$EC_b = T\theta EC_w + EC_s \qquad (10)$$

where T is a geometric factor that has a linear relationship to volumetric water content, i.e. T=α'+b'θ, in which a', b' are empirical constants for a given soil. Thus the bulk soil electrical conductivity is a $2^{nd}$ order polynomial of volumetric water content, i.e.

$$EC_b = a'EC_w\theta^2 + b'EC_w\theta + EC_s \qquad (11)$$

The expression shows good accuracy in relating soil volumetric water content and pore fluid conductivity to bulk soil electrical conductivity. The expression alone was used by others to solve for soil volumetric water content from bulk electrical conductivity measurement on soils and gave satisfactory results.

However, this equation is inadequate for application to geotechnical engineering. First, it does not account for the effect of soil skeleton density. As seen from Eq. 11, the conductivity of the soil solids is treated as a constant, which is inconsistent with the fact that the conductivity by the soil skeleton increases with the density of the material. Another problem for geotechnical applications is that conductivity is expressed in terms of volumetric water content.

In the expression for complex dielectric permittivity, the electrical conductivity is included in its imaginary part. On the other hand, we can treat dielectric constant as the imaginary part of complex electrical conductivity. This implies that soil apparent dielectric constant and bulk soil electrical conductivity follow similar rules. By this analogy, a calibration relationship for bulk soil electrical conductivity should be similar to that for soil apparent dielectric constant and can be expressed as:

$$\sqrt{EC_b}\frac{\rho_w}{\rho_d} = c + dw \qquad (12)$$

where c and d are two soil specific calibration constants.[2,6]

[2] Lin, C. P. (1999), "Time domain reflectometry for soil properties", Ph.D. Thesis, School of Civil Engineering, Purdue University, West Lafayette, Ind.
[6] Ferre, P. A., Rudolph, D. L., Kachanoski, R. G., 1996, Spatial averaging of water content by time domain reflectometry: implications for twin rod probes with and without dielectric coating. Water Resource Research, 32, 271~279.

We may express Eq. 12 in terms of volumetric water content by substituting Eq. 8

$$\sqrt{EC_b} = c\frac{\rho_d}{\rho_w} + d\theta \qquad (13)$$

and thus $$EC_b = \left(c\frac{\rho_d}{\rho_w} + d\theta\right)^2 = \left(c\frac{\rho_d}{\rho_w}\right)^2 + 2c\frac{\rho_d}{\rho_w}d\theta + d^2\theta^2 \qquad (14)$$

which is a $2^{nd}$ order polynomial for θ and is compatible with Eq. 11. Comparing the coefficient for $2^{nd}$ order term, we have $$d = \sqrt{a'EC_w} \qquad (15)$$

Thus, d is a constant that includes the effect of both soil type and pore fluid properties. Similarly, c is a constant related to dry-density-normalized conductivity of the soil solids.

There are many advantages in using the calibration equation given by Eq. 12 including: 1) the relationship is expressed in terms of gravimetric water content and thus is more suitable for geotechnical applications; 2) the expression considers both conduction from pore water and from soil particles; 3) it accounts for the density of the soil skeleton on conductivity; and 4) the expression is simple in format and easy to apply.

The relationship of Equation 12 is an important improvement over previously observed relationships. In a study on graphite-soil mixtures, it was observed that there is a reasonably good linear relationship between square root of bulk electrical conductivity and soil volumetric water content. We believe that the correlation will be improved if density effects are accounted for by use of Eq. 12.

Figure 9:
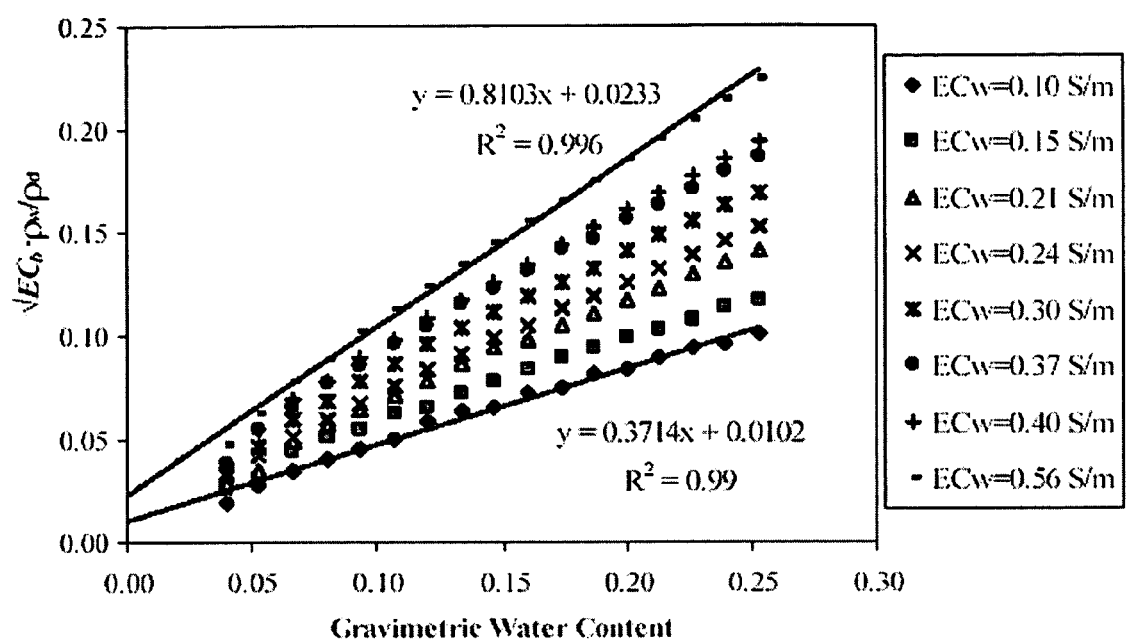
FIG. 9 shows the relationship between bulk electrical conductivity and gravimetric water content.

Using Eq. 12, data are plotted in FIG. 9.[7] These data originally were used to compare the accuracy of different models to estimate soil pore fluid conductivity from bulk electrical conductivity. FIG. 9 shows that for a given pore fluid conductivity, the square root of bulk electric conductivity has good linear relationship with gravimetric water content, with the slope of the calibration curve dependent upon the pore-fluid conductivity.

[7] Amente, G., Baker, J. M. and Reece, F. C., 2000, Estimation of Soil Solution Electrical Conductivity from Bulk Soil Electric Conductivity in Sandy Soils, Soil Sci. Soc. Am. J. 64: 1931–1939

The constants c and d for Eq. 12 can be obtained in conjunction with obtaining the calibration constants, a and b for soil apparent dielectric constant (Eq. 7) while performing laboratory compaction tests on a sample of the soil for which field measurements are to be taken. The calibration constants c and d are dependent on the conductivity of the pore fluid and will change if the pore fluid changes. In determining c and d, the pore fluid conductivity needs to be constant and within a range of 0.04~0.08 S/m and ordinary tap water is usually within this range. High pore fluid conductivity causes problems for determining $K_a$ and low pore fluid conductivity results in poor accuracy for values of c and d.

Soil apparent dielectric constant and bulk electrical conductivity are generally treated as two pieces of independent information obtained from the TDR waveform. Typically, these two pieces of information were applied separately, i.e., soil apparent dielectric constant was used to obtain soil water content while soil bulk electrical conductivity generally was used to estimate soil pore-fluid conductivity. However, these two parameters are related and their interrelationship can be utilized to simplify TDR measurements and make them more accurate.

From a theoretical point of view, soil apparent dielectric constant and bulk electrical conductivity are correlated since soil electrical conductivity is contained in the imaginary part of soil complex permittivity. A high degree of linear correlation has been found between soil apparent dielectric constant and bulk soil electrical conductivity for a broad range of soil types.

We now have two independent equations, one for soil apparent dielectric constant (Eq. 7) and one for bulk soil electrical conductivity (Eq. 12), both of which are functions of water content and dry density. Hence, they must be related to each other. Combining Eqs. 7 and 12, we get $$\sqrt{EC_b} = \frac{b \cdot c - a \cdot d}{b} \frac{\rho_d}{\rho_w} + \frac{d}{b}\sqrt{K_a} \qquad (16)$$

Equation 16 can be simplified to $$\sqrt{EC_b} = f + g\sqrt{K_a} \qquad (17)$$

in which f and g are calibration constants related to soil type and pore-fluid conductivity.

Figure 10:
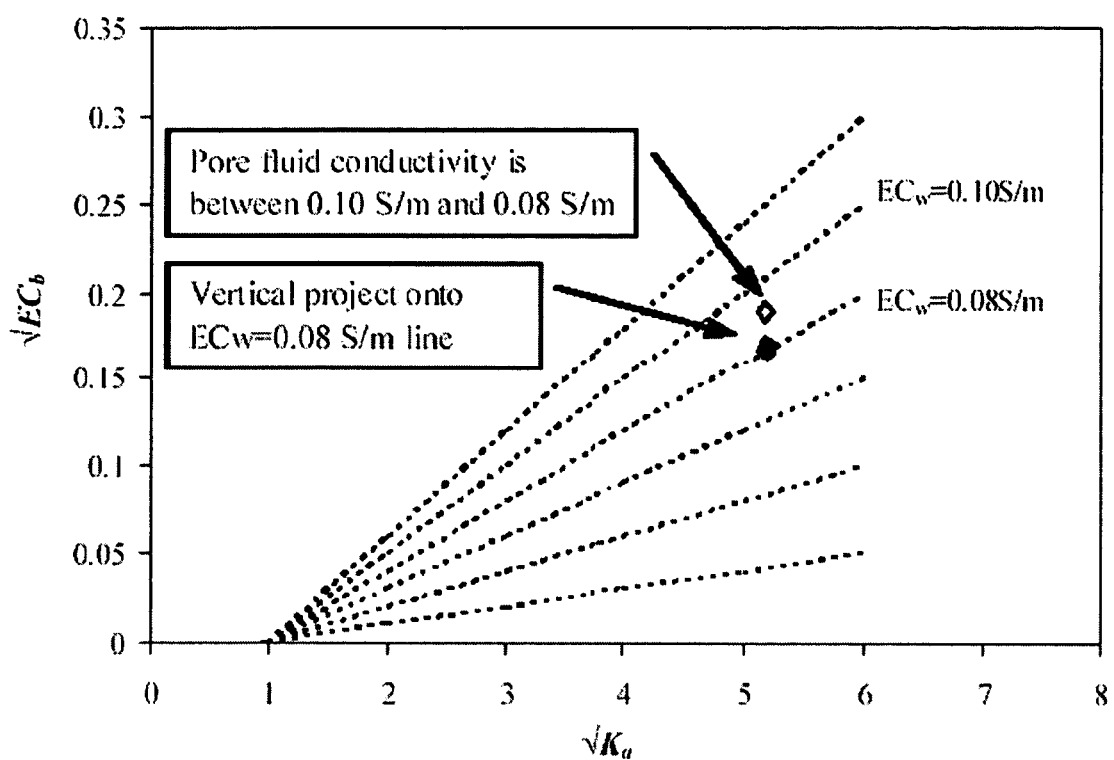
FIG. 10 shows adjustment of fluid conductivity by projecting onto laboratory calibrated relationships.

Comparing Eq. 16 with Eq. 17, we see that slope of the line g in Eq. 17 equals d/b in Eq. 16. Since both b and d are related to pore-fluid properties, the value g must also be related to them. As we have seen, b is relatively independent of ionic conductivity and d is strongly related to the conductivity of the pore fluid, thus g is predominantly dependent upon pore fluid conductivity, i.e., the slope of the line g changes systematically with pore fluid conductivity. A schematic plot of the Apparent Dielectric Constant—Electrical Conductivity calibration curves for different pore-fluid conductivities is shown in FIG. 10 where the square roots of both are plotted.

The Apparent Dielectric Constant—Electrical Conductivity calibration curve is useful for assessing the quality of a TDR measurement, e.g., values from a measurement showing large deviations from the corresponding calibration curve indicate a possible error in measurement such as caused by poor contact between the probe head and probe rods, gaps between the soil and the probe center rod, etc. Also, this calibration curve can be used to estimate the pore fluid conductivity. The most important use of the Apparent Dielectric Constant—Electrical Conductivity calibration curves is to adjust field measurements to obtain accurate values of water content and dry density as described subsequently.

Given the calibration equations relating soil apparent dielectric constant and soil bulk electric conductivity to soil water content and dry density, we can obtain soil water content and dry density by simultaneously solving Eqs. (7) and (12) which gives $$\rho_d = \frac{d\sqrt{K_a} - b\sqrt{EC_b}}{ad - cb} \qquad (18)$$

$$w = \frac{c\sqrt{K_a} - a\sqrt{EC_b}}{b\sqrt{EC_b} - d\sqrt{K_a}} \qquad (19)$$

However, water content and dry densities calculated by Eqs. 18 and 19 generally do not have satisfactory accuracy. Many factors can contribute to this inaccuracy, including random errors in dielectric constant and electrical conductivity measurements. The most significant source of error is due to differences in pore fluid conductivity between calibration samples and field samples, i.e. the pore fluid conductivity is likely to be different from that used to obtain the calibration factors. As shown earlier, the influence of pore fluid conductivity on calibration constants for $K_a$ is relatively insignificant.

Let us denote the calibration constants for electrical conductivity corresponding to the laboratory calibration test as $c_0$, $d_0$ and those corresponding to field test as $c_1$, $d_1$. Calibration constants $c_1$, $d_1$ are used in Eqs. 18 and 19 for calculating water content and dry density of the soil in the field. However, it is not practical to determine values of c and d for every conductivity likely to be encountered in the field. Our approach is to "adjust" the field situation so that the laboratory calibrations $c_0$, $d_0$ can be applied to it. By Eq. 15, the slope of the electrical conductivity calibration curve (d-value) is proportional to the square root of pore-fluid conductivity. Although pore-fluid properties in the field are unknown, we can use a systematic approach to adjust conductivity of the pore fluid in the field to the conductivity of the pore-fluid used in laboratory calibration tests, which we call the "standard pore fluid".

Suppose the calibration in laboratory is obtained with a pore fluid electrical conductivity ($EC_w$) of 0.08 Siemens/meter (S/m). A TDR test is done in the field with measured $K_a$ and $EC_b$ plotted as an open diamond in FIG. 10. There is a point with the same $K_a$ value, but with a different $EC_b$ value (indicated by solid diamond) that is located on the line from the laboratory calibration. By projecting the point corresponding to the field measurement to the lab calibration line, e.g., $EC_w$=0.08 S/m, we "replace" the sample tested in field with a virtual sample having the same water content and dry density, but with pore fluid conductivity of 0.08 S/m which equals the pore fluid conductivity used for laboratory calibration.

Thus, calibration constants determined by laboratory tests are applicable to the "adjusted sample," i.e. the dry density and water content of the "adjusted sample" can be solved using Eqs. (18) and (19) with the calibration constants from laboratory tests. Since the water content and dry density of the "adjusted sample" are the same as for the field sample, the values calculated for the "adjusted sample" apply to the field sample.

This adjustment can be made to any Apparent Dielectric Constant—Electrical Conductivity calibration line obtained from laboratory calibration. In the calibration process, we do not need to measure pore fluid conductivity, except that it should be kept constant for all calibration tests. Laboratory tests indicate that a pore fluid conductivity of 0.04~0.08 S/m works well, which is a range associated with ordinary tap water.

Equations 7, 12, and 17 provide the theoretical basis for the method of the present invention. First, the field measurement of bulk soil electrical conductivity, $EC_{b,f}$ is "adjusted" to laboratory pore-fluid conductivity using calibration Eq. 17 and the soil apparent dielectric constant, $K_{a,f}$ giving $EC_{b,adj}$. The values of $K_{a,adj}$ and $EC_{b,adj}$ are then substituted into Eqs. 18 and 19 to obtain field gravimetric water content and dry density. The data reduction process is thus:

$$\left. \begin{array}{l} K_{a,adj} = K_{a,f} \\ EC_{b,adj} = (f + g \cdot K_{a,f})^2 \end{array} \right\} \Rightarrow \begin{array}{l} \rho_d = \dfrac{d\sqrt{K_{a,adj}} - b\sqrt{EC_{b,adj}}}{ad - cb} \\ w = \dfrac{c\sqrt{K_{a,adj}} - a\sqrt{EC_{b,adj}}}{b\sqrt{EC_{b,adj}} - d\sqrt{K_{a,adj}}} \end{array} \quad (20)$$

where a, b, c, d, f and g are calibration constants obtained from laboratory compaction tests.

The method of the present invention for determining soil water content and dry density includes laboratory calibration and field application.

For lab calibration, we obtain soil-specific calibration constants a, b, c, d, f and g, which are related to soil type and pore-fluid properties. The laboratory calibration is performed in conjunction with standard compaction tests (ASTM D698 and ASTM D1557) using constant pore-fluid conductivity such as provided by tap water. Following compaction at a given water content, a central pin is driven into the mold. The MRP head is placed on the mold. The TDR reading is taken using a computer program which acquires the waveform and calculates $K_a$ and $EC_b$. After taking the readings, soil in the mold is removed and placed into an oven to obtain oven dry water content according to ASTM D2216.

Figure 11A:
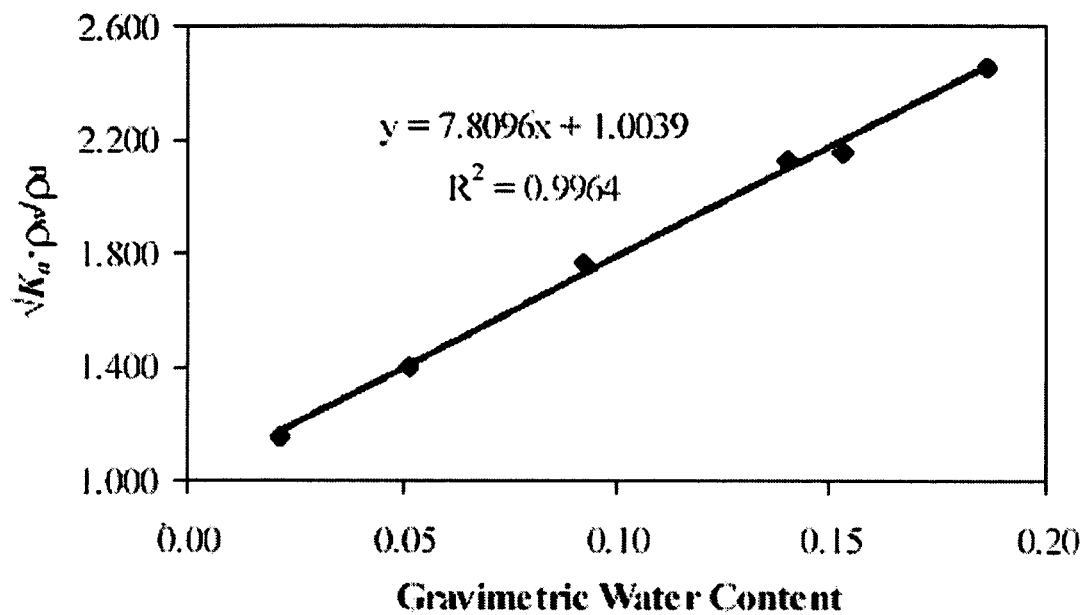
FIGS. 11a, 11b and 11c show an example of calibration on ASTM graded sand.
Figure 11B:
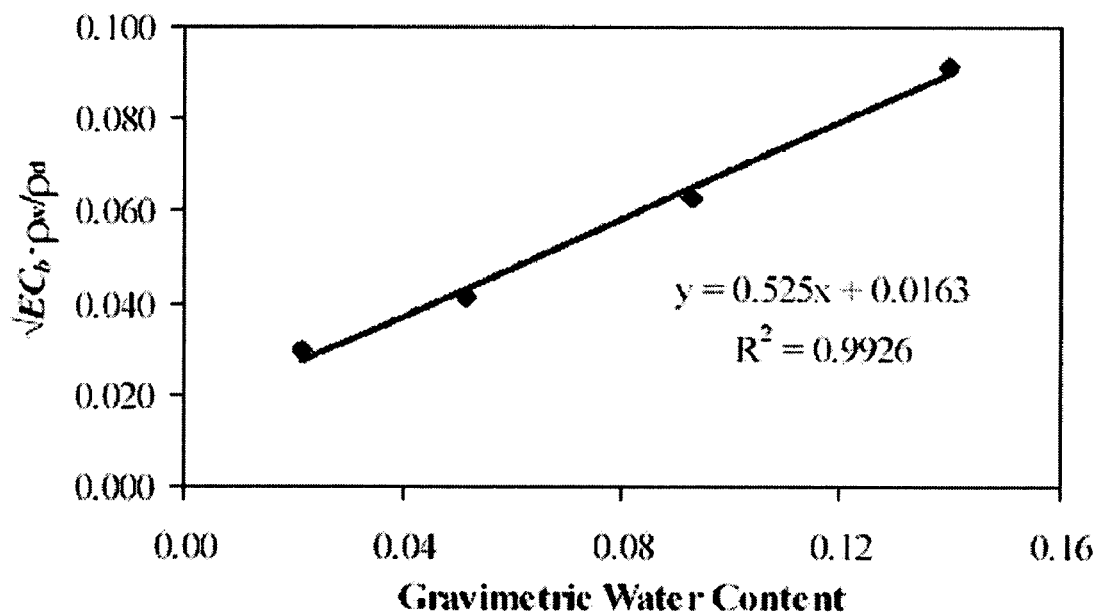
Figure 11C:
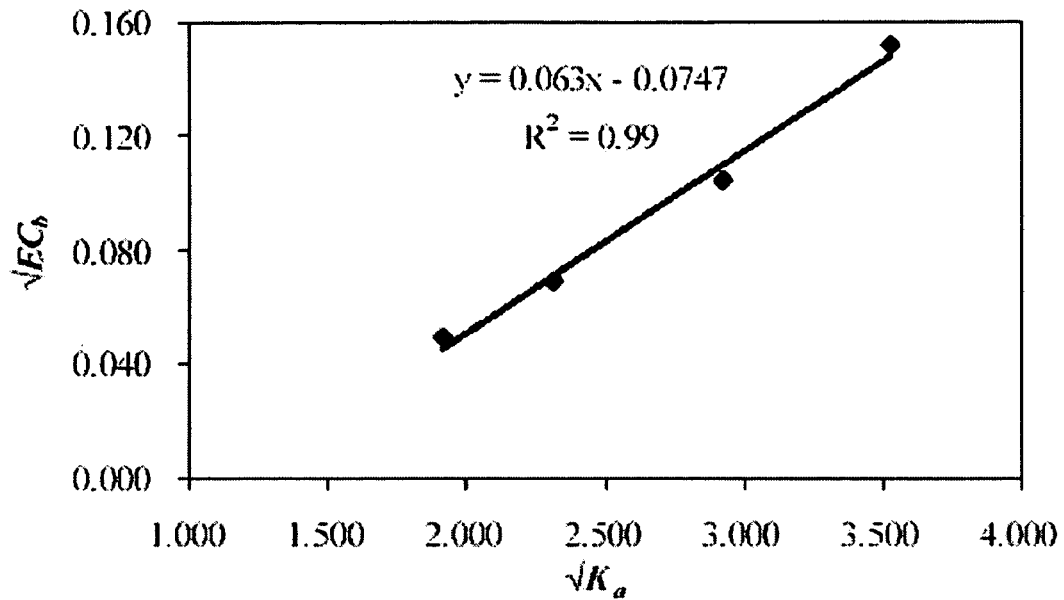

The water content, dry density, $K_a$ and $EC_b$ from a series of compaction tests at different water contents are used to obtain calibration constants a, b, c, d, f and g. The computer program has a built-in utility to calculate these calibration constants and place them into the program for use in data reduction. An example of calibration for ASTM graded sand is shown in FIGS. 11a, 11b and 11c.

The field testing procedure and test apparatus for the preferred embodiment of the present invention are somewhat similar to those specified by ASTM D6780 and described in U.S. Pat. No. 5,801,537, but without the steps of digging out the soil, compacting it in the mold, and running a second TDR field test on the soil in the mold. In summary the process according to one embodiment includes:

1) Leveling and smoothing the soil surface and placing the template on the surface.
2) Driving four spikes into the soil through holes in the guide template and removing the template.
3) Seating the MRP head on the four spikes in electrical communication.
4) Taking a TDR reading.
5) Using a computer program to apply the equations described herein to obtain $K_{a,f}$ and $EC_{b,f}$.

The program then uses the $K_{a,f}$ and $EC_{b,f}$ to obtain $K_{a,adj}$ and $EC_{b,adj}$ and calculates the field soil water content and dry density. The algorithms necessary for these calculations are described herein and may be programmed into a computer in a conventional manner. Typically it takes about 3 to 4 minutes to do a field TDR test and obtain soil water content and dry density. This is much more time efficient than the earlier TDR test (ASTM D6780) and is comparable with the time required for nuclear tests.

Measured values of soil apparent dielectric constant and bulk electrical conductivity are somewhat temperature dependent and must be accounted for if temperatures of the soil in the field are more than +/−5° C. from the temperature of the soil during calibration.

Effects of temperature on soil apparent dielectric constant differ depending on the type of soil. The apparent dielectric constant of water, $K_{a,water}$, decreases linearly from a high of about 88 near freezing to about 70 for 50° C. Others have noted that temperature effects for sandy soils behave similarly (but with reduced sensitivity) to temperature changes, but that clay soils exhibit the opposite behavior, i.e. $K_a$ increases with temperature. Our experiments on a variety of soils, each with a range of water contents and density, determined temperature effects on the apparent dielectric constant.[8] Based on this testing, we proposed adjusting the values of apparent dielectric constant from the TDR test at a given temperature to a standard temperature of 20° C. The adjusted values may be calculated from $$K_{a,20°C.} = K_{a,T} \times TCF \quad (21)$$

Where $TCF$ = Temperature Compensation Function $= 0.97 + 0.0015\, T_{test,°C.}$ for cohesionless soils, $4° C. \leq T_{test,°C.} \leq 40° C.$ $= 1.10 - 0.005\, T_{test,°C.}$ for cohesive soils, $4° C. \leq T_{test,°C.} \leq 40° C.$

[8] Dmevich, V. P., Yu, X., Lovell, J., and Tishmack, J. K., (2001a), "Temperature Effects On Dielectric Constant Determined By Time Domain Reflectometry," TDR 2001: *Innovative Applications of TDR Technology*, Infrastructure Technology Institute, Northwestern University, Evanston, Ill., September. 10 p.

From Eq. 21 it can be seen that values of $K_{a,20°C.}$ will not exceed about ten percent for extremes in temperature covered by this equation. Considering Eq. (7), we see that water content is related to the square root of $K_a$ and hence temperature effects on water content are relatively small. We believe that temperature corrections are not needed for $15°C. \leq T_{test,°C} \leq 25°C$. Also, since the dielectric constant of ice has dramatically different properties from unfrozen water, the TDR method described herein does not apply to frozen soil.

On the other hand, observed effects of temperature on soil bulk electric conductivity is consistent for both cohesive and cohesionless soils (which is different from temperature effects on $K_a$) and include: 1) at given water content, bulk soil electrical conductivity increases with temperature; 2) Compared with that for dielectric constant, the rate at which conductivity increases with temperature is more significant (e.g. 2% increase for each degree centigrade); and 3) $EC_b$ shows a linear variation with temperature for temperature ranges generally encountered in construction.[9]

[9] Rinaldi, A. V. and Cuestas, A. G.,(2002), Ohmic conductivity of a compacted silty clay, Journal of Geotechnical and Geoenvironmental Engineering, Vol. 128, No. 10, 824-835.

Developing a temperature compensation finction for bulk electrical conductivity similar to that which was done for apparent dielectric constant as discussed above would seem to be straightforward, but it is not necessary for the preferred embodiment of the method of the present invention. A scheme to account for temperature effects in the present method can be explained by use of FIG. 12 where the $\sqrt{EC_b}$ is plotted versus $\sqrt{K_a}$ for different temperatures. The long-dashed lines correspond to the relationship at 20° C. and the solid lines along the T axis represent the relationship at the temperature of the field test. The point $(EC_{b,T}, K_{a,T})$ is the data measured in the field, at temperature T. If the calibration for the $K_a$–$EC_b$ relationship was done at temperature T (denoted line 1 in the FIG. 12), adjustment to the standard pore-fluid conductivity is done as described previously. For this case, it is not necessary to make any temperature correction.

Now assume the calibration (denoted as Line 2 in FIG. 12) was conducted at room temperature (assumed to be 20° C.). It is possible to correct for temperature effects on both $K_a$ and $EC_b$ independently (denoted by paths 2–2' and 3–3' in FIG. 12), with the corresponding point (denoted 1' with coordinates $(\sqrt{EC_{b,20°C.}}, \sqrt{K_{a,20°C.}}))$ in the calibration plane for 20° C. Then, we can then apply the adjustment presented above, i.e. find point N' (with coordinates $([\sqrt{EC_{b,20°C.}}]_{adj}, \sqrt{K_{a,20°C.}}))$ and make final computations using Eq. 20.

Figure 12:
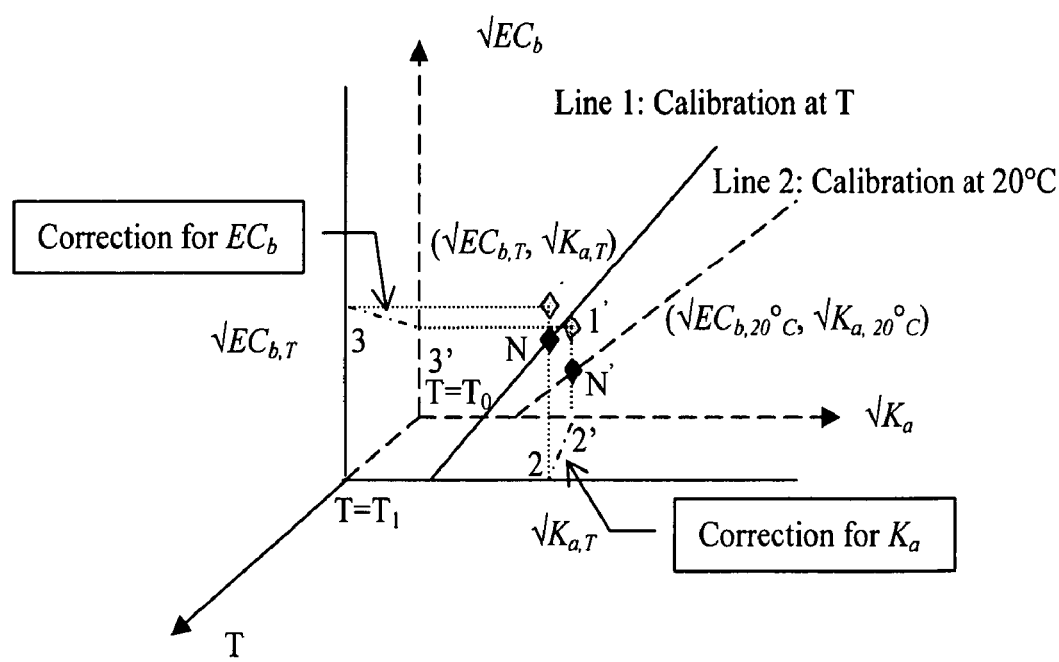
FIG. 12 shows a schematic presentation of temperature correction.

A closer look at FIG. 12 indicates that the points 2', 1' and N' are located on the same vertical line. This means that given the calibration line at 20° C., we can find point N' by using point 2' alone. Thus, we only need to compensate for temperature effects on $K_a$ using Eq. 21, i.e. correcting $K_{a,T}$ to $K_{a,20°C.}$ (points 2 to 2' in FIG. 12) and then moving vertically to point N' which gives the values for making final computations using Eq. 20.

Tests were conducted on an ASTM graded sand to verify this adjustment for temperature effects. Standard compaction tests using ASTM D698 were conducted on the sand. The specimens were then sealed by plastic wrap and placed successively in rooms with controlled temperatures of 1° C., 7° C., 22° C., 30° C., and 40° C. TDR readings were taken after temperatures in the specimen stabilized. Afterwards, the entire soil specimen was oven-dried to determine soil water content by ASTM D2216.

Figure 13:
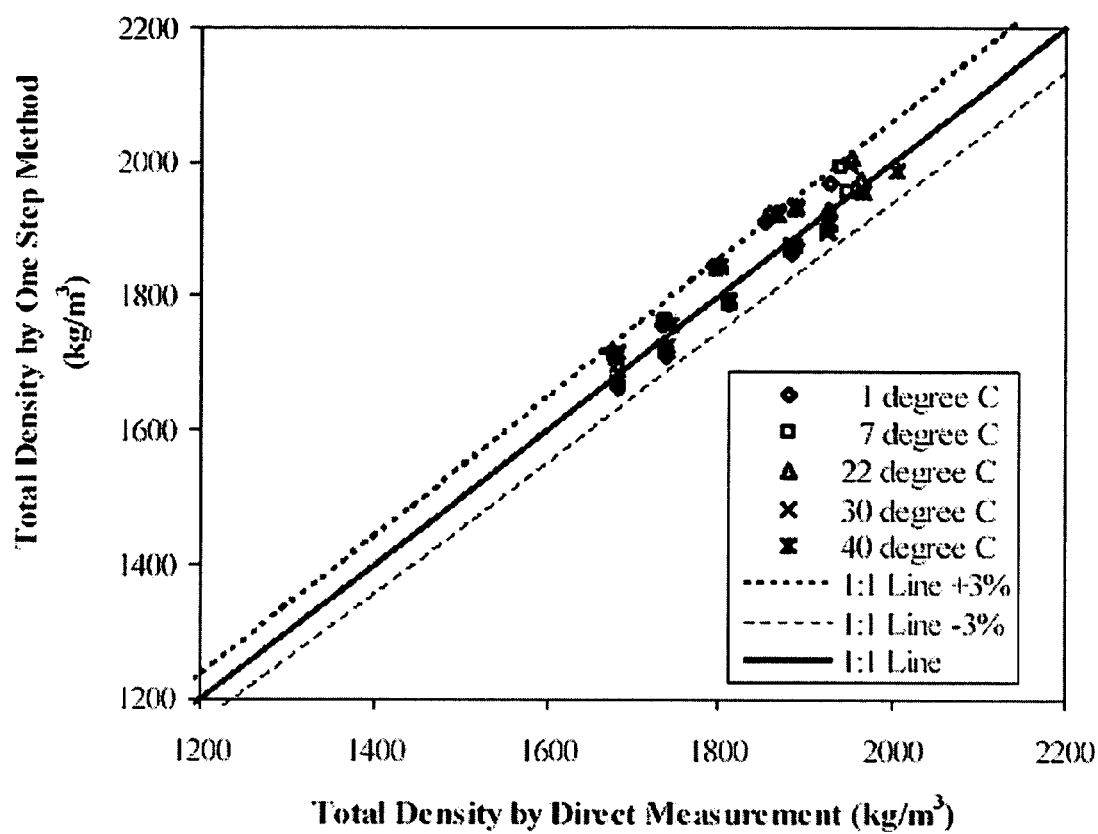
FIG. 13 shows the results of applying a simplified temperature correction approach on ASTM sand.

Results of data reduction by this temperature compensation approach are shown in FIG. 13 and lie within +/−3% of the Total Density by Direct Measurement which indicate this approach for temperature compensation provides satisfactory accuracy.

The present method for determining soil water content and dry density as described above was applied to data obtained from 192 laboratory and field tests. The data represent a variety of soils including dense-graded aggregate bases, sands, silts, clays, stabilized soils, and a low density mixed waste. Water contents determined by the present method generally fell within ±1 percentage points of oven-dry water contents while dry densities generally fell within ±3% of the dry densities determined by direct measurement and oven dry water content. Both measurements provide sufficient accuracy for use in construction quality control. The method of the present invention makes the water content and dry density measurements on the same sample and appears to be applicable to a wide variety of soils commonly encountered in field.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

We claim:

1. A method for measuring dry density and gravimetric water content of soil, comprising the steps of:
   providing a plurality of spikes adapted to be driven into the soil;
   driving said plurality of spikes into the soil in spaced relationship;
   applying to said plurality of spikes an electrical signal suitable for time domain reflectometry;
   analyzing a reflected signal using time domain reflectometry to determine an apparent dielectric constant $K_a$ of the soil and bulk electrical conductivity $EC_b$ of the soil;
   calculating dry density $P_d$ of the soil using a predetermined relationship between $K_a$, $EC_b$ and $\rho_d$; and
   calculating gravimetric water content w of the soil using a predetermined relationship between $K_a$, $EC_b$, and w.

2. The method of claim 1, wherein the soil has a surface and the plurality of spikes have a lower end, and the step of analyzing a reflected signal includes measuring the apparent distance between a signal reflected from the surface of the soil and a signal reflected from the lower end of said plurality of spikes to determine an apparent length La.

3. The method of claim 2, wherein said plurality of spikes have a probe length Lp and the apparent dielectric constant $K_a = (La/Lp)^2$.

4. The method of claim 1, wherein the step of analyzing a reflected signal includes measuring a source voltage Vs of the applied signal and a long term voltage Vf of the reflected signal.

5. The method of claim 4, wherein the bulk electrical conductivity $EC_b = (1/C)(Vs/Vf - 1)$ where C is a constant related to probe length Lp.

6. The method of claim 1, wherein the predetermined relationship between $K_a$, $EC_b$ and $\rho_d$ is $$\rho_d = \frac{d\sqrt{K_a} - b\sqrt{EC_b}}{ad - cb},$$

where a, b, c and d are soil specific calibration constants.

7. The method of claim 6, wherein calibration constants a and b are predetermined experimentally for a given soil using the relationship $$\sqrt{K_a}\frac{\rho_w}{\rho_d} = a + bw,$$

where $\rho_w$ is the density of water, $\rho_d$ is the dry density of the soil, and w is the gravimetric water content of the soil.

8. The method of claim 7, wherein $EC_b$ is replaced with an adjusted value $EC_{b,\,adj}$ for which calibration constants c and d are known.

9. The method of claim 1, wherein the predetermined relationship between $K_a$, $EC_b$ and w is $$w = \frac{c\sqrt{K_a} - a\sqrt{EC_b}}{b\sqrt{EC_b} - d\sqrt{K_a}},$$

where a, b, c and d are soil specific calibration constants.

10. The method of claim 9, wherein calibration constants c and d are predetermined experimentally for a given soil using the relationship $$\sqrt{EC_b}\frac{\rho_w}{\rho_d} = c + dw,$$

where $\rho_w$ is the density of water, $\rho_d$ is the dry density of the soil, and w is the gravimetric water content of the soil.

11. The method of claim 10, wherein $EC_b$ is replaced with an adjusted value $EC_{b,\,adj}$ for which calibration constants c and d are known.

12. The method of claim 11, wherein the calculated value of $K_a$ at a given temperature is adjusted to a value $K_{a,20°\,C.}$ at a standard temperature of 20° C., where $$K_{a,20°\,C.} = K_{a,T} \times TCF$$

and where

TCF = Temperature Compensation Function $= 0.97 + 0.0015\, T_{test,°\,C.}$ for cohesionless soils, $4°\,C. \leq T_{test,°\,C.} \leq 40°\,C.$ $= 1.10 - 0.005\, T_{test,°\,C.}$ for cohesive soils, $4°\,C. \leq T_{test,°\,C.} \leq 40°\,C.$

13. A method for measuring dry density of soil, comprising the steps of:
providing a plurality of spikes adapted to be driven into the soil;
driving said plurality of spikes into the soil in spaced relationship;
applying to said plurality of spikes an electrical signal suitable for time domain reflectometry;
analyzing a reflected signal using time domain reflectometry to determine an apparent dielectric constant $K_a$ of the soil and bulk electrical conductivity $EC_b$ of the soil; and
calculating dry density $\rho_d$ of the soil using a predetermined relationship between $K_a$, $EC_b$ and $\rho_d$.

14. The method of claim 13, wherein the predetermined relationship between $K_a$, $EC_b$ and $\rho_d$ is $$\rho_d = \frac{d\sqrt{K_a} - b\sqrt{EC_b}}{ad - cb},$$

where a, b, c and d are soil specific calibration constants.

15. The method of claim 14, wherein calibration constants a and b are predetermined experimentally for a given soil using the relationship $$\sqrt{K_a}\frac{\rho_w}{\rho_d} = a + bw,$$

where $\rho_w$ is the density of water, $\rho_d$ is the dry density of the soil, and w is the gravimetric water content of the soil.

16. The method of claim 14, wherein calibration constants c and d are predetermined experimentally for a given soil using the relationship $$\sqrt{EC_b}\frac{\rho_w}{\rho_d} = c + dw,$$

where $\rho_w$ is the density of water, $\rho_d$ is the dry density of the soil, and w is the gravimetric water content of the soil.

17. The method of claim 14, wherein $EC_b$ is replaced with an adjusted value $EC_{b,\,adj}$ for which calibration constants c and d are known.

18. The method of claim 17, wherein the calculated value of $K_a$ at a given temperature is adjusted to a value $K_{a,20°\,C.}$ at a standard temperature of 20° C., where and where TCF = Temperature Compensation Function $= 0.97 + 0.0015\, T_{test,°\,C.}$ for cohesionless soils, $4°\,C. \leq T_{test,°\,C.} \leq 40°\,C.$ $= 1.10 - 0.005\, T_{test,°\,C.}$ for cohesive soils, $4°\,C. \leq T_{test,°\,C.} \leq 40°\,C.$

19. A method for measuring gravimetric water content of soil, comprising the steps of:
providing a plurality of spikes adapted to be driven into the soil;
driving said plurality of spikes into the soil in spaced relationship;
applying to said plurality of spikes an electrical signal suitable for time domain reflectometry;
analyzing a reflected signal using time domain reflectometry to determine an apparent dielectric constant $K_a$ of the soil and bulk electrical conductivity $EC_b$ of the soil; and
calculating gravimetric water content w of the soil using a predetermined relationship between $K_a$, $EC_b$, and w.

20. The method of claim 19, wherein the predetermined relationship between $K_a$, $EC_b$ and w is w $$w = \frac{c\sqrt{K_a} - a\sqrt{EC_b}}{b\sqrt{EC_b} - d\sqrt{K_a}},$$

where a, b, c and d are soil specific calibration constants.

21. The method of claim 20, wherein calibration constants a and b are predetermined experimentally for a given soil using the relationship $$\sqrt{K_a}\frac{\rho_w}{\rho_d} = a + bw,$$

where $\rho_w$ is the density of water, $\rho_d$ is the dry density of the soil, and w is the gravimetric water content of the soil.

22. The method of claim 20, wherein calibration constants c and d are predetermined experimentally for a given soil using the relationship $$\sqrt{EC_b}\frac{\rho_w}{\rho_d} = c + dw,$$

where $\rho_w$, is the density of water, $\rho_d$ is the dry density of the soil, and w is the gravimetric water content of the soil.

23. The method of claim 22, wherein $EC_b$ is replaced with an adjusted value $EC_{b,adj}$ for which calibration constants c and d are known.

24. The method of claim 23, wherein the calculated value of $K_a$ at a given temperature is adjusted to a value $K_{a,20°C}$ at a standard temperature of 20° C., where $$K_{a,20°C.} = K_{a,T=TCF}$$

and where $$TCF = \text{Temperature Compensation Function}$$
$$= 0.97 + 0.0015\, T_{test,°C.} \text{ for cohesionless soils,}$$
$$4° \text{ C.} \leq T_{test,°C.} \leq 40° \text{ C.}$$
$$= 1.10 - 0.005\, T_{test,°C.} \text{ for cohesive soils,}$$
$$4° \text{ C.} \leq T_{test,°C.} \leq 40° \text{ C.}$$

25. An apparatus for measuring dry density of soil, comprising:
   a plurality of spikes adapted to be driven into the soil in spaced relationship;
   means for applying to said plurality of spikes an electrical signal suitable for time domain reflectometry;
   means for analyzing a reflected signal using time domain reflectometry to determine an apparent dielectric constant $K_a$ of the soil and bulk electrical conductivity $EC_b$ of the soil; and
   means for calculating dry density $\rho_d$ of the soil using a predetermined relationship between $K_a$, $EC_b$ and $\rho_d$.

26. The apparatus of claim 25, wherein the predetermined relationship between $K_a$, $EC_b$ and $\rho_d$ is $$\rho_d = \frac{d\sqrt{K_a} - b\sqrt{EC_b}}{ad - cb},$$

where a, b, c and d are soil specific calibration constants.

27. The apparatus of claim 26, further comprising means for calculating gravimetric water content w of the soil using a predetermined relationship between $K_a$, $EC_b$, and w.

28. The apparatus of claim 25, further comprising means for compensating for soil temperature.

29. An apparatus for measuring gravimetric water content of soil, comprising:
   a plurality of spikes adapted to be driven into the soil in spaced relationship;
   means for applying to said plurality of spikes an electrical signal suitable for time domain reflectometry;
   means for analyzing a reflected signal using time domain reflectometry to determine an apparent dielectric constant $K_a$ of the soil and bulk electrical conductivity $EC_b$ of the soil; and
   means for calculating gravimetric water content w of the soil using a predetermined relationship between $K_a$, $EC_b$, and w.

30. The apparatus of claim 29, wherein the predetermined relationship between $K_a$, $EC_b$ and w is $$w = \frac{c\sqrt{K_a} - a\sqrt{EC_b}}{b\sqrt{EC_b} - d\sqrt{K_a}},$$

where a, b, c and d are soil specific calibration constants.

31. The apparatus of claim 29, further comprising means for compensating for soil temperature.

32. The method of claim 13, wherein said predetermined relationship includes a difference between a function of $K_a$ and a function of $EC_b$.

33. The method of claim 32, wherein $EC_b$ is adjusted to reflect a predetermined soil pore fluid electrical conductivity.

34. The method of claim 13, wherein $EC_b$ is adjusted to reflect a predetermined soil pore fluid electrical conductivity.

35. The method of claim 19, wherein said predetermined relationship includes a difference between a function of $K_a$ and a function of $EC_b$.

36. The method of claim 35, wherein said predetermined relationship includes a ratio of said difference and a second difference between a function of $K_a$ and a function of $EC_b$.

37. The method of claim 36, wherein $EC_b$ is adjusted to reflect a predetermined soil pore fluid electrical conductivity.

38. The method of claim 19, wherein $EC_b$ is adjusted to reflect a predetermined soil pore fluid electrical conductivity.

* * * * *